(12) United States Patent
Vieira

(10) Patent No.: US 6,501,906 B2
(45) Date of Patent: Dec. 31, 2002

(54) EVAPORATION DEVICE FOR VOLATILE SUBSTANCES

(75) Inventor: Pedro Queiroz Vieira, Parede (PT)

(73) Assignee: C.T.R. Consultoria Tecnica e Representacoes Lda, Almargem do Bispo (PT)

(*) Notice: Subject to any disclaimer, the term of this patent is extended or adjusted under 35 U.S.C. 154(b) by 0 days.

(21) Appl. No.: 09/994,032

(22) Filed: Nov. 21, 2001

(65) Prior Publication Data

US 2002/0076214 A1 Jun. 20, 2002

Related U.S. Application Data

(63) Continuation-in-part of application No. 09/919,125, filed on Jul. 31, 2001, and a continuation-in-part of application No. 09/918,898, filed on Jul. 31, 2001, which is a continuation-in-part of application No. 09/739,981, filed on Dec. 18, 2000.

(30) Foreign Application Priority Data

Apr. 5, 2001 (EP) ............................................. 01107795
Apr. 5, 2001 (EP) ............................................. 01107796

(51) Int. Cl.[7] ................................................. F24F 6/00
(52) U.S. Cl. ................................................... 392/395
(58) Field of Search ................................. 392/386, 390, 392/391, 392, 394, 395; 261/139, 142, 94, 95, 104, DIG. 65; 219/543, 544, 546, 547, 548

(56) References Cited

U.S. PATENT DOCUMENTS 3,414,864 A * 12/1968 Barrington .................... 29/620
4,498,071 A * 2/1985 Plough et al. .......... 204/192.21
5,222,186 A * 6/1993 Schimanski et al. ........ 392/392
6,236,807 B1 * 5/2001 Ruffolo et al. ............... 392/390

FOREIGN PATENT DOCUMENTS

| EP | 0 362 397 A1 | 4/1990 | ............ A01M/1/20 |
|---|---|---|---|
| EP | 0 451 331 A1 | 10/1991 | .......... A45D/34/02 |
| EP | 0 591 537 A1 | 4/1994 | ............ H01C/7/02 |
| EP | 0 911 041 A | 4/1999 | |
| EP | 0 943 344 A | 9/1999 | |
| EP | 0 962 132 A | 12/1999 | |
| EP | 0 998 947 A1 | 5/2000 | ............. A61L/9/03 |
| EP | 1 055 430 A | 11/2000 | |
| JP | 58135183 | 8/1983 | |
| WO | WO 98/19526 | 5/1998 | |
| WO | WO 98/58692 | 12/1998 | |
| WO | WO 01/05442 A | 1/2001 | |

* cited by examiner

Primary Examiner—Sang Paik
(74) Attorney, Agent, or Firm—McNair Law Offices, P.A.; Cort Flint

(57) ABSTRACT

The present invention relates to an evaporation device 1 for volatile substances, in particular insecticides and/or aromatics, which includes a housing 2 and a heating unit 10 located therein. Heating Unit 10 comprises a heating block 11 in which an electric resistance element 15 is contained for heating. In addition device 1 includes a container 3 that can be connected to housing 2 for a substance to be evaporated. A wick 6 can be inserted into the container with a wick end 8 protruding from the container 3 for the evaporation of the substance contained in the container 3 to be heated by the heating unit. According to the invention, electric resistance element 15 advantageously includes a rod-shaped resistance body 17 coated, at least in some areas, with a resistance layer 16 that is cut to provide a predetermined resistance value according to the composition of the substance to be evaporated. In this manner, a heating unit 10 with small dimensions and miniaturized evaporation device 1 is provided for the evaporation of volatile substances.

19 Claims, 3 Drawing Sheets

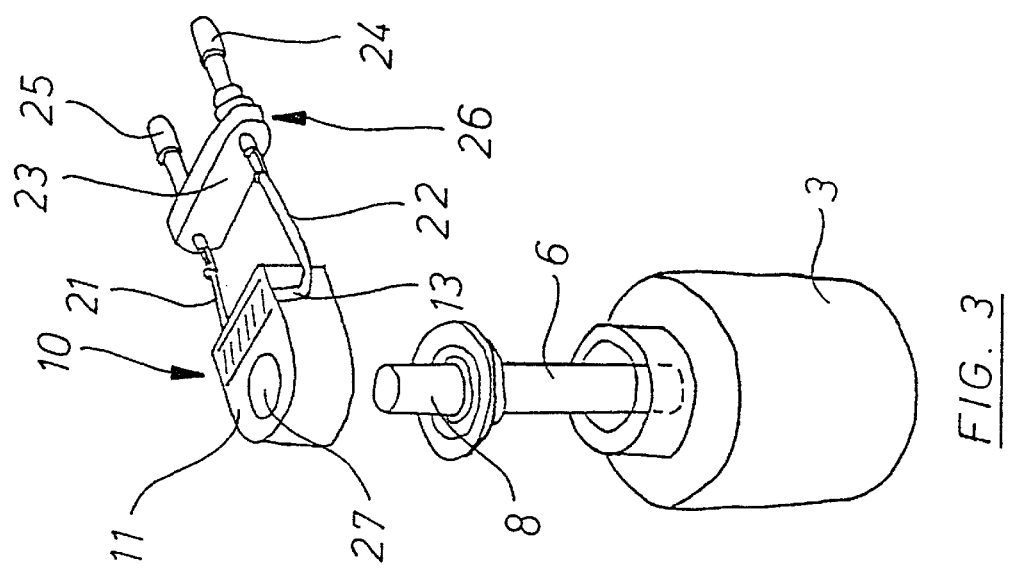
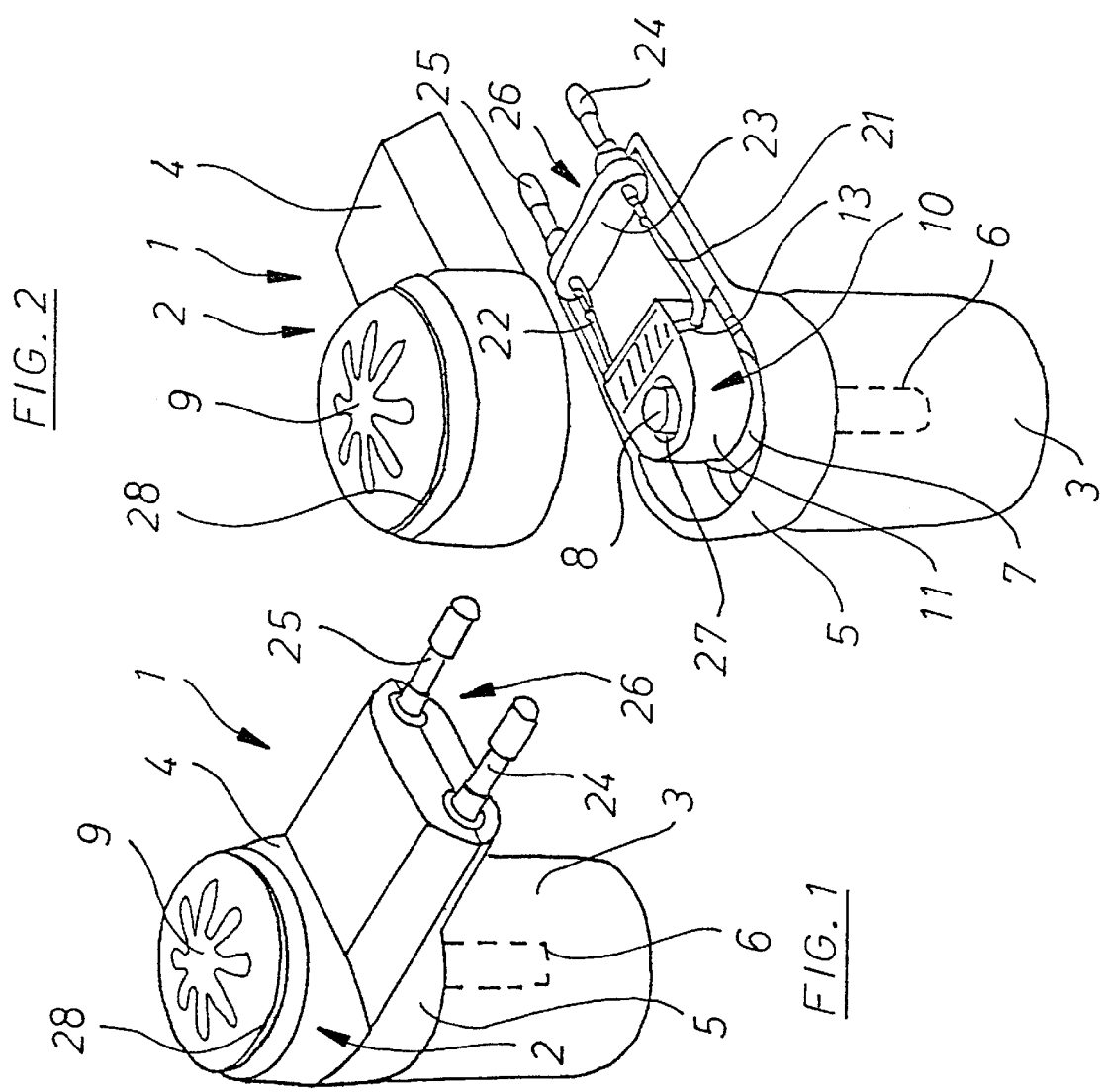

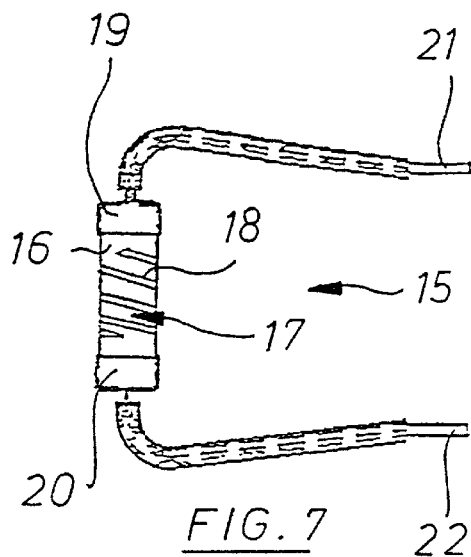
FIG. 7
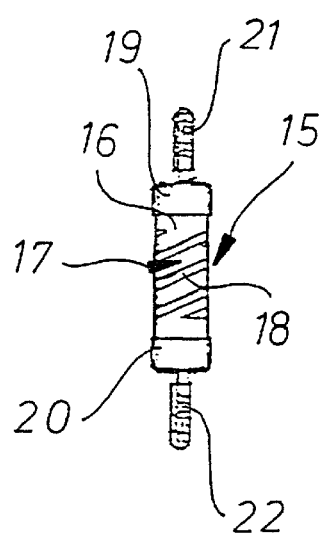
FIG. 8
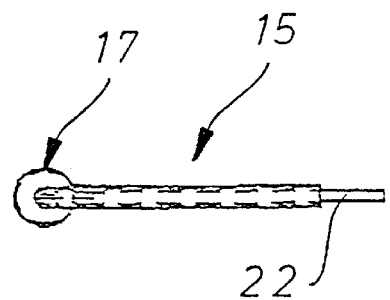
FIG. 9
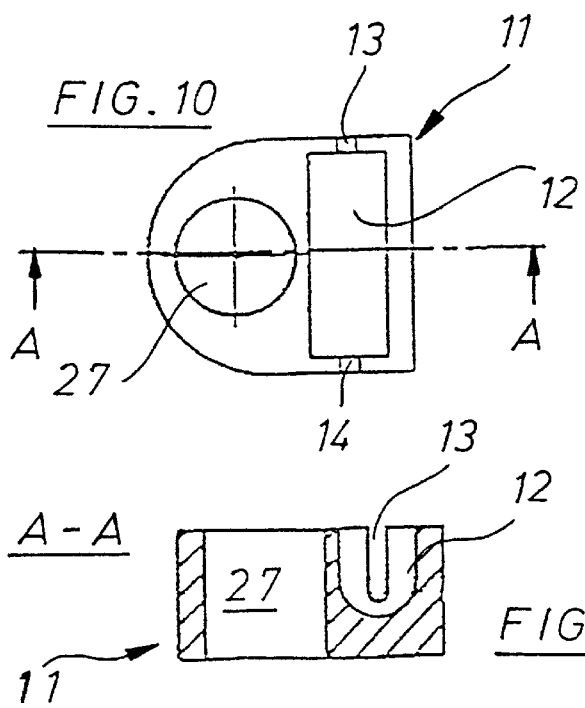
FIG. 10
A-A
FIG. 11
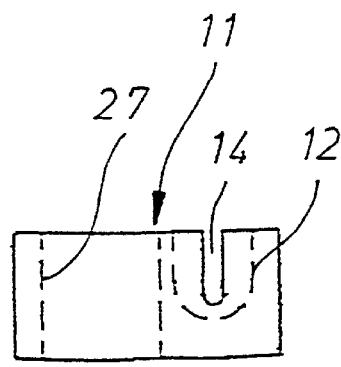
FIG. 12

EVAPORATION DEVICE FOR VOLATILE SUBSTANCES

This is a continuation-in-part of U.S. application Ser. No. 09/919,125 filed on Jul. 31, 2001, and U.S. application Ser. No. 09/918,898 filed on Jul. 31, 2001, which are continuation-in-parts of application Ser. No. 09/739,981 filed on Dec. 18, 2000.

BACKGROUND OF THE INVENTION

The present invention relates to a device to evaporate volatile substances, in particular insecticides and/or aromatics according to the introductory clause of claim 1. Devices for evaporation are generally known. For example, evaporation devices are known where a small plate is introduced into an evaporation device which is impregnated with an active ingredient and heated in order to evaporate the active ingredient. Furthermore a method is also known by which a container containing a volatile substance is introduced into a housing of an evaporation device. This container comprises a wick that conveys the substance to be evaporated by means of capillary action out of the container. Whereby the wick end protruding from the container is located next to a heating element such as e.g., a ceramic block, so that the substance is evaporated through the heat radiated by the ceramic block. The evaporated substance can escape from the housing into the environment through aeration slits in the housing.

Another example, an evaporation device for volatile substances, in particular insecticides and/or aromatics, is known from EP 0 943 344 A1 that includes a housing with a heating unit installed therein. The heating unit comprises a heating block made of a ceramic material connected via electric lines to a connection plug located on the housing. An electrical resistance element is contained in the housing to heat the heating block. A container connected to the housing, for a substance to be evaporated, whereby a wick can be inserted into the container; with the container being connected to the housing. The wick is associated with the heating unit for the evaporation of the substance in the container by a wick end protruding from the container into the heating element. The evaporation device includes a plug-in part with a connection plug. The plug-in part is provided with threads and is inserted into the housing in which the container is disposed. Pin openings are provided on the housing into which snap-in pins are inserted in such manner that they engage the threads of the plug-in part. The distance between the heating unit carried by the plug-in part and a wick end protruding from the container can be changed by turning the plug-in part. In an embodiment of this system the plug-in part can furthermore be mounted in an eccentric manner in the housing, so the relative distance between the wick end and the heating unit can be changed in function of the desired degree of evaporation. The heating unit includes a ceramic block with an electric resistance element. Commercially available, relatively large as resistance elements are used. This leads to a relatively large heating unit and thereby also a great space requirement of the housing surrounding the heating unit and of the overall evaporation device. Such space-consuming evaporation devices are less attractive visually and can disturb the general visual effect, e.g. in a living room. In addition the design employs a great number of components which leads to large which is also relatively expensive and complicated to manufacture.

Furthermore the evaporation temperature cannot be sufficiently regulated because of the utilization of commercial resistance elements and this may have a negative effect on the flammability of certain parts or of the entire evaporation device, and possibly also on the degree of evaporation. A similar design with the above-mentioned disadvantages is also known from WO 98/58692 and EP 0 962 132 A1.

Accordingly, an object of the present invention is to create an inexpensive evaporation device for the evaporating of volatile substances, such as insecticides and/or aromatics, or relatively small dimensions in which the evaporation temperature can be accurately regulated according to the substance to be evaporated.

SUMMARY OF THE INVENTION

The above objectives are accomplished according to the present invention by utilizing the electric resistance element to constitute a heating unit of small size and thereby to provide an overall miniaturized of the evaporation device, preferably, the heating element includes a rod-shaped resistance body coated at least in some areas with a resistance layer that is cut and/or ground into certain areas for the selection of a given resistance value corresponding to the composition of the substance to be evaporated.

A resistance element of this type for heating units can advantageously be of relatively small size so that the heating block, the heating unit, and the entire housing containing the heating unit may have a relatively small size. In this manner, miniaturized evaporation devices can be had with which one or two or more suitably adapted low-volume containers may be accommodated in the housing. Due to the reduced expenditure for material and components, the miniaturized evaporation device can be produced relatively simply and inexpensively as a disposable item.

Another important advantage of an evaporation device according to the invention is that the evaporation temperature can be adjusted optimally according to the composition of the substance to be evaporated. Advantageously, the resistance layer for a given resistance value may be cut or ground in the element at different locations. The danger of flammability of the device is thus reduced and the possible negative effect on the degree of evaporation can be avoided.

There are, in principle, different ways for notching or grinding the resistance layer in order to provided a desired resistance value. In a preferred embodiment, the resistance layer is cut into and around the rod-shaped, preferably cylindrical, resistance body in a helicoidal form, such as by helicoidal laser cutting. With such a helicoidal cut the resistance value can be adjusted very precisely and easily for optimal evaporation performance.

The resistance layer can, in principle also be made of different materials, e.g. in form of a special metal layer. In an especially preferred embodiment, the resistance layer is however made in form of a metal oxide layer, preferably a nickel-chrome alloy layer. Such a metal oxide layer may be advantageously burned on thermo-chemically, e.g. by vacuum metallizing or cathodic sputtering in form of a thin layer. When the resistance layer has been applied, it is preferably subjected to a thermal process in order to stabilize the resistance layer. In addition, or alternately, the resistance body can be made of ceramic, preferably with a high content in $AL_2O_3$ (aluminum oxide), so that an especially good heat conductivity of the resistance body and thereby of the resistance element overall is achieved. The content in $AL_2O_3$ depends on the actual installation conditions e.g. the housing material, the wick material, etc. being used.

Advantageously, metal caps may be placed on the ends of the coated, rod-shaped resistance body, which are preferably pressed on. An electrical line is preferably welded to each of these caps and is in turn connected to the connection plug. Copper wire with good electrical conductivity is preferably used for the electric lines. A good electrical contact with the resistance layer is furthermore easily and reliably achieved with the metal caps. In principle several ways exist for the installation of the rod-shaped resistance element on the heating block. In an advantageous embodiment, the rod-shaped resistance element can be inserted into a recess in the heating block. The resistance element is encapsulated in the recess using there in a highly heat-conductive material in order to fix the resistance element securely in the heating block. The encapsulating material may have a great heat conductivity may be a flame-resistant insulation cement. Furthermore a slit is preferably formed on either side of the resistance element, at the opposite ends of the recess, whereby the electrical lines can be routed out of the heating block to the connection plug. With a design of this type the resistance element can easily be inserted into the recess during assembly, e.g. also using a clamping lock, so that the resistance element cannot slip during the encapsulating process. In addition, electric lines can easily be curved in the direction of the connection plug. The electric lines can be insulated in a conventional manner.

An advantageous, compact design can be provided by making the length of the resistance element, as seen in the longitudinal direction of the recess approximately equal to the width of the heating block. In this case, the electric lines may be bent at the caps approximately at right angles to the resistance element. The lines may then extend approximately parallel to each other and approximately in line with the two plug-in connections of the connection plug. Such an alignment of the electrical lines achieves an especially compact design of the heating unit, and this contributes in minimizing the size of the housing and the entire evaporation device.

In yet another aspect of the invention, a wick opening, preferably a passage hole or a traversing indentation on the edge of the heating block is formed into which the wick end extends is formed in the heating block next to the electrical resistance element. By means of such a wick opening a simple and reliable attribution of the wick end to the heating block and thereby to the heating unit is possible, and this contributes in ensuring effective evaporation.

An especially easy and rapid assembly of the heating unit in the housing is possible by providing the housing in at least two parts, an upper shell and a lower shell. The upper and lower shells can be connected to each other by means of a snap-in and/or clipping elements. Preferably, the connection means, e.g. snap-in elements, to are formed in the lower shell. At least one of the two shells is provided with aeration slits to let the evaporated substance escape into the environment. The aeration slits may be located above the wick end in the upper shell. Such a two-part housing can be produced very simply and inexpensively.

The connection plug preferably includes a base plate from which the plug pins extend to which the electric lines are connected. The base plate together with other components may be located in the housing and clamped between the upper shell and the lower shell for a strong, and thus chatter-free fixed positioning. This makes a design of great value which is overall very stable, as well as secure in fixing the components in predetermined positions.

In order to give the evaporation device a visually more esthetic aspect, a decorative element can be attached to the upper shell. A surrounding edge border is preferably formed on the upper shell, to which such a decorative element can be snapped or clipped on. Such a decorative element could for example be in form of a flowering blossom.

DESCRIPTION OF THE DRAWINGS

The invention will be more readily understood from a reading of the following specification and by reference to the accompanying drawings forming a part thereof, wherein an example of the invention is shown and wherein:

FIG. 1 shows a schematic perspective view of the miniaturized evaporation device according to the invention;

FIG. 2 shows a schematic perspective representation of the evaporation device of FIG. 1 with the upper shell of the two-part housing lifted off;

FIG. 3 shows a schematic perspective representation of a container, a wick and a heating unit of the evaporation device shown in FIGS. 1 and 2;

FIG. 7 shows an enlarged schematic top view of a resistance element with electric lines;

FIG. 8 shows a schematic back view of the resistance element of FIG. 7;

FIG. 9 shows a schematic lateral view of the resistance element of FIG. 7;

FIG. 10 shows a schematic enlarged top view of a heating block made in the form of a ceramic body;

FIG. 11 shows a schematic sectional view along line A—A of FIG. 10; and,

FIG. 12 shows a schematic lateral view of the representation of FIG. 10.

DESCRIPTION OF A PREFERRED EMBODIMENT

Figure 4:
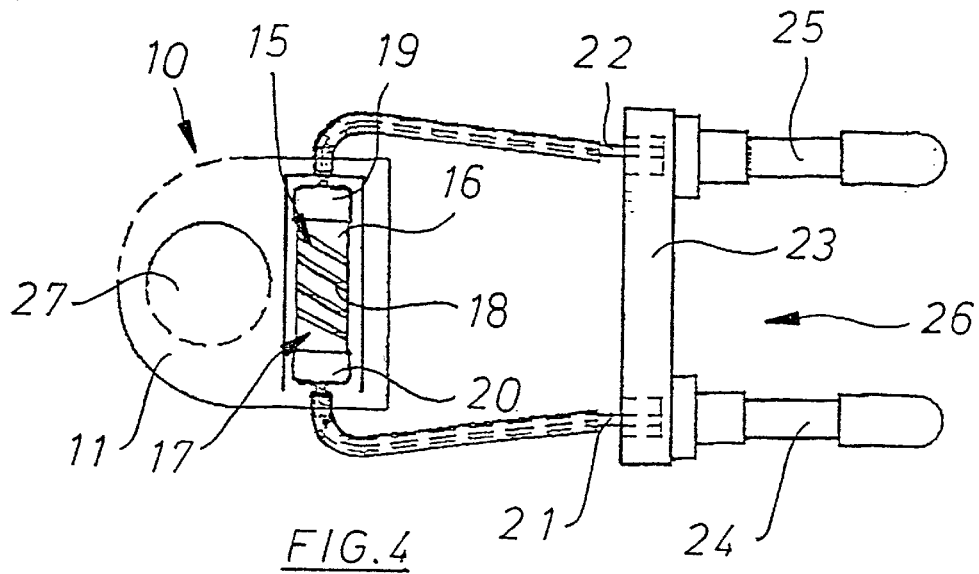
FIG. 4 shows an enlarged top view of the heating unit of FIG. 3.

Referring now in more detail to the drawings, the invention will now be described in more detail.

As can best be seen in FIG. 1 is a miniaturized evaporation device 1 is illustrated with a housing 2 and a container 3 for a substance to be evaporated. The container 3 can be snapped onto the housing 2 using any suitable clip connection, for example.

As can be seen in from FIG. 2, evaporation device 1 is illustrated for the sake of clarity without housing 2, wherein a wick 6 can be inserted by means of a wick holder 7 into the container 3. Wick 6 a wick end 8 from the container 3 into the housing 2, as can again be seen in FIG. 2. Upper shell 4 is provided with aeration slits 9 in an area above the wick end 8 to allow the escape of the evaporated substance.

Figure 5:
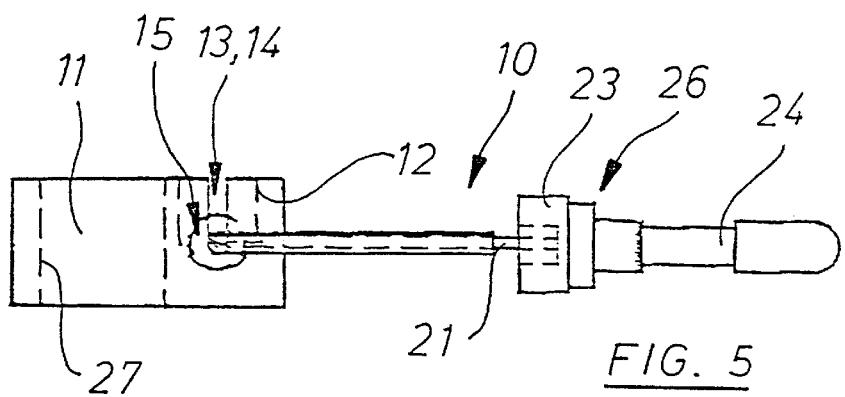
FIG. 5 shows a schematic lateral view of the heating unit of FIG. 4.
Figure 6:
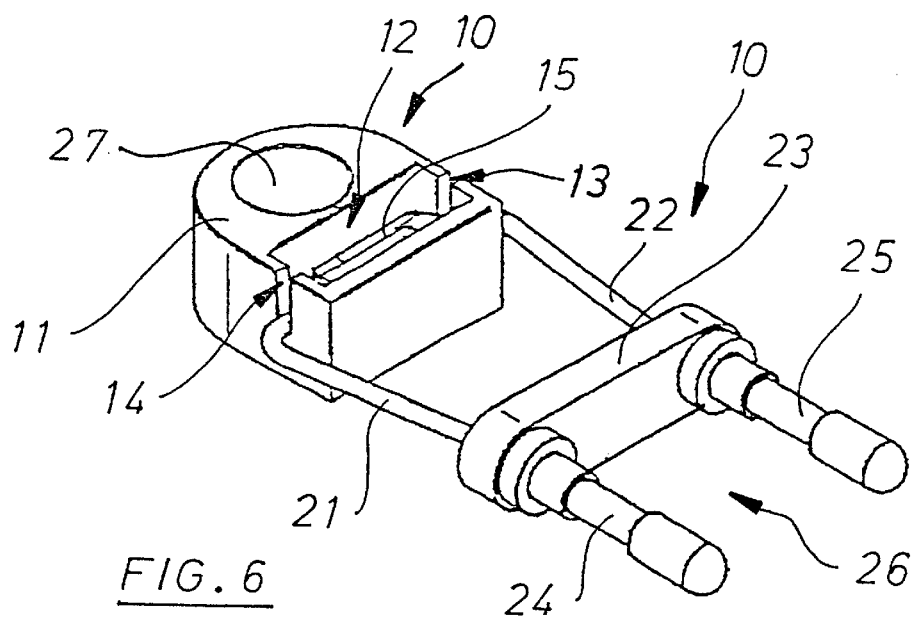
FIG. 6 shows a schematic, perspective representation of the heating unit of FIGS. 4 and 5.

As can further be seen in FIGS. 2 and 3, evaporation device 1 comprises a heating unit 10 that is illustrated enlarged in FIGS. 4 to 6.

As best can be seen from FIGS. 4, 5, and 6, heating unit 10 comprises a ceramic block 11 in which an opening 12 is made. In each of the lateral sides of the block, a slit 13, 14 is provided. FIGS. 10 to 12 show ceramic block 11 in different views illustrating the geometry of the opening 12 as well as of the slits 13, 14. Thus opening 12, as seen in cross-section, is U-shaped. This shape is merely selected as an example. Ceramic block 11 preferably has a maximum width and length of e.g., 116 mm and a height of 9 mm.

A rod-shaped resistance element 15 is inserted into block opening 12. Resistance element 15 includes a resistance body 17 coated with a metal oxide resistance layer 16 (not shown in detail) to provide a heating unit 10 of small overall dimensions. To provide a predetermined resistance value, resistance layer 16 may consist of a metal oxide, e.g. a nickel-chrome alloy, which is cut into helicoidally, e.g. by laser spiral cutting. A helicoidal Cut 18 is thus produced around the rod-shaped cylindrical resistance body 17. FIGS. 7 to 9 show the resistance element 15 in different views, without attachment to a connection plug 26.

Resistance body 17 is preferably made of ceramic, with a given content of $Al_2O_3$ for the provision of good heat conductivity characteristics. For example, resistance body 17 has a length of approximately 10 mm and a diameter of approximately 3 mm. At each end of coated, cylindrical resistance body 17 a metal cap 19, 20 is installed, preferably pressed on. To these caps 19, 20 an electric line 21, 22, preferably a copper wire with insulation is welded to caps 19 and 20.

As can be seen in particular from FIGS. 4 to 6, the resistance element 15 is inserted into the opening 12, whereby the two electric lines 21, 22 are passed through the slits 13, 14 out of the ceramic block 11. Following this the resistance element 15 is encapsulated in a highly heat conductive, flame resistant insulation cement in order to fix the resistance element 15 in the ceramic block 11 while maintaining its good heat conductivity.

As FIGS. 4 to 6 further show, the length of resistance element 15 in the longitudinal direction of opening 12 is approximately equal to the width of ceramic block 11. Electric lines are then angled approximately at a right angle to resistance element 15 and parallel to each other. The lines are in-line with two plug-in pins 24, 25 of connection plug 26 as they extend to a base plate 23 of connection plug 26. This provides for a design with overall little space requirements, making a miniaturized construction of evaporation device 1 possible, as shown in approximately actual size in the drawings of FIGS. 1 to 2.

As can further be seen in FIG. 10, a circular wick opening 27 is provided in ceramic block 11 next to opening 12, into which wick end 8 extends in the assembled evaporation device, as can be seen in particular in FIG. 2. In its assembled state, heating unit 10, as well as the base plate 23 of connection plug 26, is clamped between upper shell 4 and lower shell 5. As is shown merely as an example, a surrounding edge border 28 is formed on the upper shell, to which a decorative element with a corresponding counter-element can be snapped in, e.g. a decorative element in form of a flowering bloom (not shown).

While a preferred embodiment of the invention has been described using specific terms, such description is for illustrative purposes only, and it is to be understood that changes and variations may be made without departing from the spirit or scope of the following claims.

What is claimed is:

1. An evaporation device for volatile substances such as insecticides, aromatics, and the like comprising:
   a housing;
   a heating unit disposed in said housing having a heating block;
   an electric resistance element carried by said heating block to heat the heating block;
   a container for a substance to be evaporated to be carried by said housing;
   a wick inserted into said container having a wick end protruding from the container for the evaporation of the substance in said container;
   said electric resistance element including a rod-shaped resistance body coated in at least some areas with a resistance layer said resistance layer being processed by one of cutting and grinding in some areas to provide a desired resistance value according to the evaporation temperature required for evaporation of the substance in said container so that a heating unit with small dimensions and miniaturized evaporation device are provided.

2. The device of claim 1 wherein said resistance layer is cut around said rod-shaped resistance body in a form of a spiral.

3. The device of claim 2 wherein said layer is a metal oxide layer and said resistance body is made of a ceramic material.

4. The device of claim 3 wherein said metal oxide is a nickel/chrome alloy and said ceramic material has a high content of $Al_2O_3$.

5. The device of claim 1 including a metal cap carried on each end of said rod-shaped resistance body for attachment to a plurality of electric lines coupled to a connection plug.

6. The device of claim 5 wherein said rod-shaped resistance element is inserted into an opening formed in said heating block, and is encapsulated in said opening material by having a high heat conductivity, and slits are formed in said heating block through which said electric lines are routed out of the heating block to said connection plug.

7. The device of claim 6 wherein a length of said resistance element as seen in a longitudinal direction of said opening is approximately equal to a width of said heating block so that the electric lines may be bent approximately at a right angle relative to said resistance element near said caps to extend approximately parallel to each other as well as approximately in line with plug pins of the connection plug.

8. The device of claim 7 wherein said connection plug comprises a base plate from which the plug pins extend on one side and to which the electric lines are connected on the other side.

9. The device of claim 8 including an upper shell and a lower shell wherein said base plate of said connection plug and said heating unit are clamped between the upper shell and the lower shell.

10. The devices of claim 1 including a wick passage formed in said heating block near said electric resistance element through which said wick end extends.

11. The device of claim 1 wherein said housing includes an upper shell and a lower shell which can be connected to each other by a retaining element and one of said upper and lower shells including aeration openings above said wick end to allow the evaporated substance to escape.

12. The device of claim 11 including a decorative element attached on a surrounding edge border of said upper shell.

13. A miniaturized evaporation device for volatile substances such as insecticides, aromatics, and the like of the type which includes a housing; a heating unit disposed in said housing having a heating block and an electric resistance element carried by said heating block to heat the heating block; a container for a substance to be evaporated carried by said housing; and a wick inserted into said container having a wick end extending from the container for the evaporation of the substance in said container; wherein the improvement comprises:
   a heating unit including an electric resistance element which includes a rod-shaped resistance body coated in at least some areas with a processed resistance layer;
   said processed resistance layer being processed in prescribed layer areas to provide a desired resistance value according to the evaporation temperature required for evaporation of the volatile substance in said container so that a heating unit with small dimensions and miniaturized evaporation device are provided;

a housing having an upper shell;

said container for containing said volatile substance carried by said housing; and said heating unit being carried between said upper shell and said container.

14. The device of claim 13 wherein said heating unit includes a heating block having a wick passage disposed between said upper and lower shells; and said wick end extending through said wick passage.

15. The device of claim 14 wherein said heating element is carried by said heating block near said wick passage for heating said wick end.

16. The device of claim 13 wherein said resistance layer is processed by one of cutting and grinding in some areas to provide said desired resistance value.

17. The device of claim 13 wherein said layer is a metal ox de layer and said resistance body is made of a ceramic material.

18. The device of claim 17 wherein a helix is formed into said resistance layer by said process.

19. The device of claim 13 wherein said housing includes said upper shell and a lower shell which can be connected to each other by a retaining element and one of said upper and lower shells including aeration openings above said wick end to allow the evaporated substance to escape.

* * * * *

(12) INTER PARTES REEXAMINATION CERTIFICATE (0344th)
United States Patent
Vieira

(10) Number: US 6,501,906 C1
(45) Certificate Issued: Feb. 14, 2012

(54) EVAPORATION DEVICE FOR VOLATILE SUBSTANCES

(75) Inventor: Pedro Queiroz Vieira, Parede (PT)

(73) Assignee: C.T.R., Almargem do Bispo (PT)

Reexamination Request:
No. 95/000,372, Jul. 23, 2008

Reexamination Certificate for:
Patent No.: 6,501,906
Issued: Dec. 31, 2002
Appl. No.: 09/994,032
Filed: Nov. 21, 2001

Related U.S. Application Data

(63) Continuation-in-part of application No. 09/919,125, filed on Jul. 31, 2001, now Pat. No. 6,487,367, and a continuation-in-part of application No. 09/918,898, filed on Jul. 31, 2001, now Pat. No. 6,563,091, which is a continuation-in-part of application No. 09/739,981, filed on Dec. 18, 2000, now Pat. No. 6,446,583.

(51) Int. Cl.
*A01M 1/20* (2006.01)
*A61L 9/015* (2006.01)
*A61L 9/03* (2006.01)
*F24F 6/00* (2006.01)

(52) U.S. Cl. ........................................ 392/395
(58) Field of Classification Search .................. None
See application file for complete search history.

(56) References Cited

To view the complete listing of prior art documents cited during the proceeding for Reexamination Control Number 95/000,372, please refer to the USPTO's public Patent Application Information Retrieval (PAIR) system under the Display References tab.

*Primary Examiner* — Catherine S. Williams

(57) ABSTRACT

The present invention relates to an evaporation device 1 for volatile substances, in particular insecticides and/or aromatics, which includes a housing 2 and a heating unit 10 located therein. Heating Unit 10 comprises a heating block 11 in which an electric resistance element 15 is contained for heating. In addition device 1 includes a container 3 that can be connected to housing 2 for a substance to be evaporated. A wick 6 can be inserted into the container with a wick end 8 protruding from the container 3 for the evaporation of the substance contained in the container 3 to be heated by the heating unit. According to the invention, electric resistance element 15 advantageously includes a rod-shaped resistance body 17 coated, at least in some areas, with a resistance layer 16 that is cut to provide a predetermined resistance value according to the composition of the substance to be evaporated. In this manner, a heating unit 10 with small dimensions and miniaturized evaporation device 1 is provided for the evaporation of volatile substances.

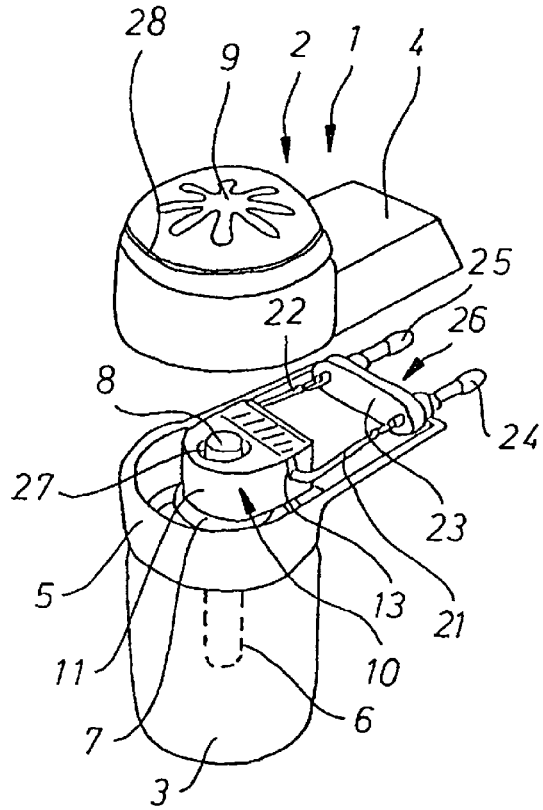

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-19 are cancelled.

* * * * *